United States Patent [19]

Preijde

[11] Patent Number: 5,895,363
[45] Date of Patent: Apr. 20, 1999

[54] DEVICE FOR PERFORMING EQUILIBRIUM EXERCISES

[76] Inventor: Thomas Quirinus Maria Preijde, Huizen, 1275 DK, Radboud 11, Netherlands

[21] Appl. No.: 08/817,427
[22] PCT Filed: Oct. 5, 1995
[86] PCT No.: PCT/NL95/00338
§ 371 Date: Jun. 18, 1997
§ 102(e) Date: Jun. 18, 1997
[87] PCT Pub. No.: WO96/11725
PCT Pub. Date: Apr. 25, 1996

[30] Foreign Application Priority Data

Oct. 17, 1994 [NL] Netherlands ............... 9401712

[51] Int. Cl.$^6$ ........................................ A63B 23/02
[52] U.S. Cl. ............... 600/595; 600/587; 434/258; 482/909
[58] Field of Search ................ 482/909; 273/431, 273/460; 473/207, 208, 209, 211; 600/587, 592, 594, 595; 434/255, 258, 247; 33/379, 383, 384, 387, 388, 511, 515

[56] References Cited

U.S. PATENT DOCUMENTS

| | | |
|---|---|---|
| 1,962,256 | 6/1934 | Nelson et al. . |
| 3,099,245 | 7/1963 | Deaner . |
| 3,178,187 | 4/1965 | Cardwell . |
| 3,955,562 | 5/1976 | Farrar, Jr. ............... 600/595 |
| 4,096,637 | 6/1978 | Stade .................... 33/383 |
| 4,298,201 | 11/1981 | Palinkas . |
| 4,493,328 | 1/1985 | Saito ................... 473/209 |
| 4,528,990 | 7/1985 | Knowles ................ 600/587 |
| 5,209,470 | 5/1993 | Cimaroli et al. ......... 33/379 |
| 5,300,921 | 4/1994 | Hoch . |
| 5,373,858 | 12/1994 | Rose et al. ............. 600/595 |
| 5,425,378 | 6/1995 | Swezey et al. .......... 600/595 |
| 5,755,623 | 5/1998 | Mizenko ............... 33/384 |

FOREIGN PATENT DOCUMENTS

| | | |
|---|---|---|
| 0349074 | 1/1990 | European Pat. Off. . |
| 2227938 | 12/1973 | Germany . |
| 9219333 | 11/1992 | WIPO . |

Primary Examiner—Jeanne M. Clark
Attorney, Agent, or Firm—Webb Ziesenheim Bruening Logsdon Orkin & Hanson, P.C.

[57] ABSTRACT

The invention relates to a device for performing equilibrium exercises which includes a fitting assembly for fitting the device to a part of the body, for instance the head, of a user and a position indicating assembly connected to the fitting assembly for indicating the position of the device. The position indicating assembly is herein observable by the user and can be formed by a conventional or electronic spirit level instrument.

20 Claims, 2 Drawing Sheets

DEVICE FOR PERFORMING EQUILIBRIUM EXERCISES

BACKGROUND OF THE INVENTION

1) Field of the Invention

The invention relates to a device for performing equilibrium exercises, comprising means for fitting, thereof to a part of the body of a user and means connected to the fitting means and observable by the user for indicating the position of the device. Such a device is known e.g. from DE-A-2 227 938.

2) Background Art

In physiotherapy much use is made of equilibrium exercises in order to check the action of the equilibrium coordination system of a patient and, if possible, to correct it. This equilibrium coordination system can be disrupted in various ways. The equilibrium organs themselves may for instance function poorly, although it may also be the case that the equilibrium organs function properly per se, but that there is an inadequate motor coordination between these organs and the body parts with which the patient tries to maintain his balance. In the usual exercises the patient is placed on an unstable surface and possible deficiencies in attempts by the patient to preserve his equilibrium are determined by the physiotherapist. A drawback of this known exercise method is that as a result of the long route between the equilibrium organs and the body parts responsible for maintaining equilibrium, possible disturbances in the equilibrium coordination system are difficult to localize.

The above mentioned prior art document DE-A-2 227 938 already describes a device for performing biodynamic reaction training according to the so called Alexander technique, comprising means which are attached to the body of the user, and which allow the user to visually monitor the posture of his head with regard to his neck. In a first embodiment these posture monitoring means comprise a pair of mirrors arranged on the shoulders of the user on either side of his head, and a third mirror which is suspended from his head in front of his eyes, and which allows the user to see the side mirrors in order to check his posture. In alternative embodiment use is made of for instance a fibre optic system to transmit a view from the side of the head to the eyes of the user, or a mini TV-camera arranged on the shoulder, which is connected to a monitor arranged in front of the user. This known device however is only suitable for checking the posture of the head with regard to the torso of the user, and cannot be used for any other kind of equilibrium exercises.

SUMMARY OF THE INVENTION

The invention therefore has for its object to provide a device with which disturbances in the equilibrium coordination system can be detected and localized rapidly and in simple manner. For this purpose the invention provides a device for performing equilibrium exercises of the type described above, wherein the position indicating means comprise a spirit level instrument. By making use of position indicating means which are connected directly to the body of the user or patient and which can be observed by himself, a direct feedback of deviations from the equilibrium position is obtained outside the equilibrium coordination system, thereby enabling a simpler detection and analysis of possible disturbances in the equilibrium coordination system.

Furthermore, by using a spirit level instrument for indicating the position, a small and lightweight device is obtained, which is suited to a large number of different equilibrium exercises.

Preferred embodiments of the training device according to the invention are described in the dependent claims.

BRIEF DESCRIPTION OF THE DRAWING

The invention is now elucidated in the light of an embodiment, wherein reference is made to the annexed drawings, FIGS. 1 and 2, which are perspective views of a device according to the invention fitted to the head of a patient.

DETAILED DESCRIPTION OF THE PREFERRED EMBODIMENT

Figure 1:
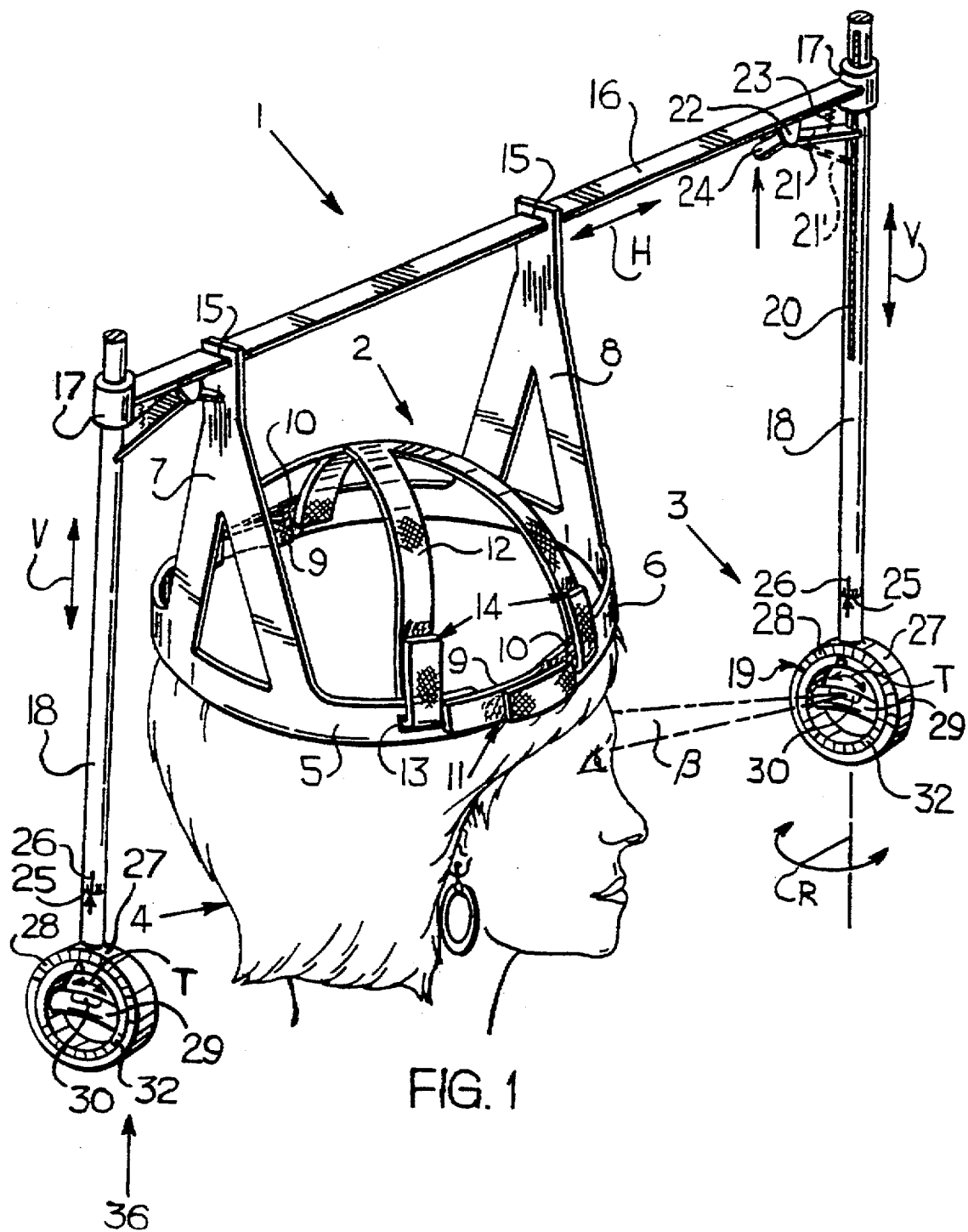

A device 1 for performing equilibrium exercises comprises means 2 for fitting the device to a body part, in the example shown here the head 4 of a user, and means 3 connected to the fitting means for indicating the position of the device. The position indicating means 3 can be observed by the user, and in the case shown here they are visible in that they lie within the field of vision B of the user.

The fitting means 2 comprise a head-band which is assembled from two parts 5, 6 and provided with two uprights 7, 8 formed integrally with the corresponding head-band parts 5, 6. The head-band part 5, 6 and upright 7, 8 connected thereto are made of a relatively rigid but light weight material, such as for example a suitable plastic or light metal. The head-band is adjustable, in order to enable fitting on heads of different dimensions. To this end the rear band part 5 is provided with two fastening strips 9 which can be passed through slot 10 arranged in the front band part 6 and, once the band has been placed at the correct diameter, can then be fastened by means of a Velcro tape connection 11. In order to prevent the band dropping down over the head 4 it is further provided with an adjustable cross-piece 12, two legs of which are fixed to the two band parts 5, 6 while the two free legs can be placed through openings 13 arranged in the band parts 5, 6 and, after being set to the correct length, can be closed using a Velcro tape connection 14.

The uprights 7, 8 are each provided at their top with a slot 15 through which is placed a profiled suspension strip 16 with T-shaped profiled. The strip 16 is movable in the direction of the arrow H in order to vary the distance between the position indicating means 3 and the head 4 of the user. The leg 31 of the T-shaped strip 16 can take a toothed form whereby strip 16 can be fixed in a specific position. In order to be able to read the set position of the strip 16, it can be provided with a calibration (not shown), for instance in centimeters, reckoned from the outer end of strip 16.

At the outer end of the strip 16 remote from the user is arranged a sleeve 17 in which a suspension rod 18 is received slidably in the direction of the arrow V. The suspension rod 18 carries at its bottom end a spirit level instrument 19 which provides the actual position indication. In order to enable fixing of suspension rod 18, and therewith the spirit level instrument 19, at a determined height, the suspension rod 18 is provided with a gear rack 20 which co-acts with the free end of a lever 21 which is hingedly connected to strip 16 by means of a hinge 22. The lever 21 is biased by a tension spring 23 to the position shown in which it engages into the gear rack 20 of suspension rod 18. By depressing a control part 24 of lever 21 in the direction of the arrow counter to the bias of spring 23, the lever is moved to the position 21' drawn with dashed lines, whereby it is taken out of engagement with gear rack 20 and the rod 18 can be moved up and downward. For reading a set height of the suspension rod 18 a calibration can be arranged (not shown here), which indicates for example the distance in centimeters from the middle point of the spirit level instrument 19.

By means of a rotation pivot 25 the spirit level instrument 19 is rotatable on the longitudinal axis of the suspension rod 18 in the direction of the arrow R. In order to determine the angle of rotation, the suspension rod 18 is provided with a calibration 26. The spirit level instrument 19 is further rotatable round an axis lying transversely of the lengthwise axis of rod 18 (arrow T). For this purpose the spirit level instrument has an annular peripheral part 32 which is received for rotation in an outer ring 27 arranged on the underside of rod 18. This outer ring 17 is provided with a calibration 28 for setting the angle of rotation of the spirit level instrument 19. The latter comprises in per se known manner a transparent tube body 29 partially filled with liquid while leaving free an air bubble 30 functioning as indicator. When the device 1 is intended for use by children, a toy figure can for instance be used instead of an air bubble 30. All that is important is that the indicator floats in the liquid. In the embodiment shown the tube body 29 otherwise displays an arcuate form, wherein the convex side of the body 29 faces downward. The state of equilibrium of the air bubble 30 is hereby unstable so that only a slight deviation from this equilibrium position will result in a relatively rapid and great movement of the air bubble 30. The device is thus very sensitive.

The operation of the training device is now as follows. Once the fitting means 2 have been arranged on the head 4 of the user and are fastened comfortably but stably on the head 4 by adjusting the various bands, a suitable rest position of the spirit level instrument 19 is adjusted by sliding the strip 16 and the suspension rod 18, and turning the rotation pivot 25 and the inner ring 32. This position wherein the spirit level instrument 19 must in any case be readable for the user, depends on the exercises to be performed. For some exercises it is desirable to place the spirit level 19 at the height of the equilibrium organs, while it may be desirable for other exercises to place the spirit level on an imaginary axis for a movement to be performed during these exercises. In the shown position the spirit level instrument 19 can be used to visualize movements of the head 4 on an axis running roughly parallel to the imaginary connecting line between the spirit level instrument 19 and the head 4.

It may however also be desirable to visualize movements in a plane defined by the strip 16 and the suspension rod 18. For this purpose the spirit level instrument 19 can be rotated through 90° on the rotation pivot 25 and provided with a mirror directed toward the user (not shown here). The user can thus still observe the movements of the indicator air bubble 30 in the spirit level instrument 19.

The response speed of the spirit level instrument 19 can be adapted by adding damping means. For users who have difficulty with rapid movements, the spirit level instrument can thus be filled for instance with a highly viscous liquid, whereby the air bubble 30 will move comparatively slowly therein. Other slowing mechanisms such as for instance an upward directed curvature of the spirit level can of course be envisaged.

Figure 2:
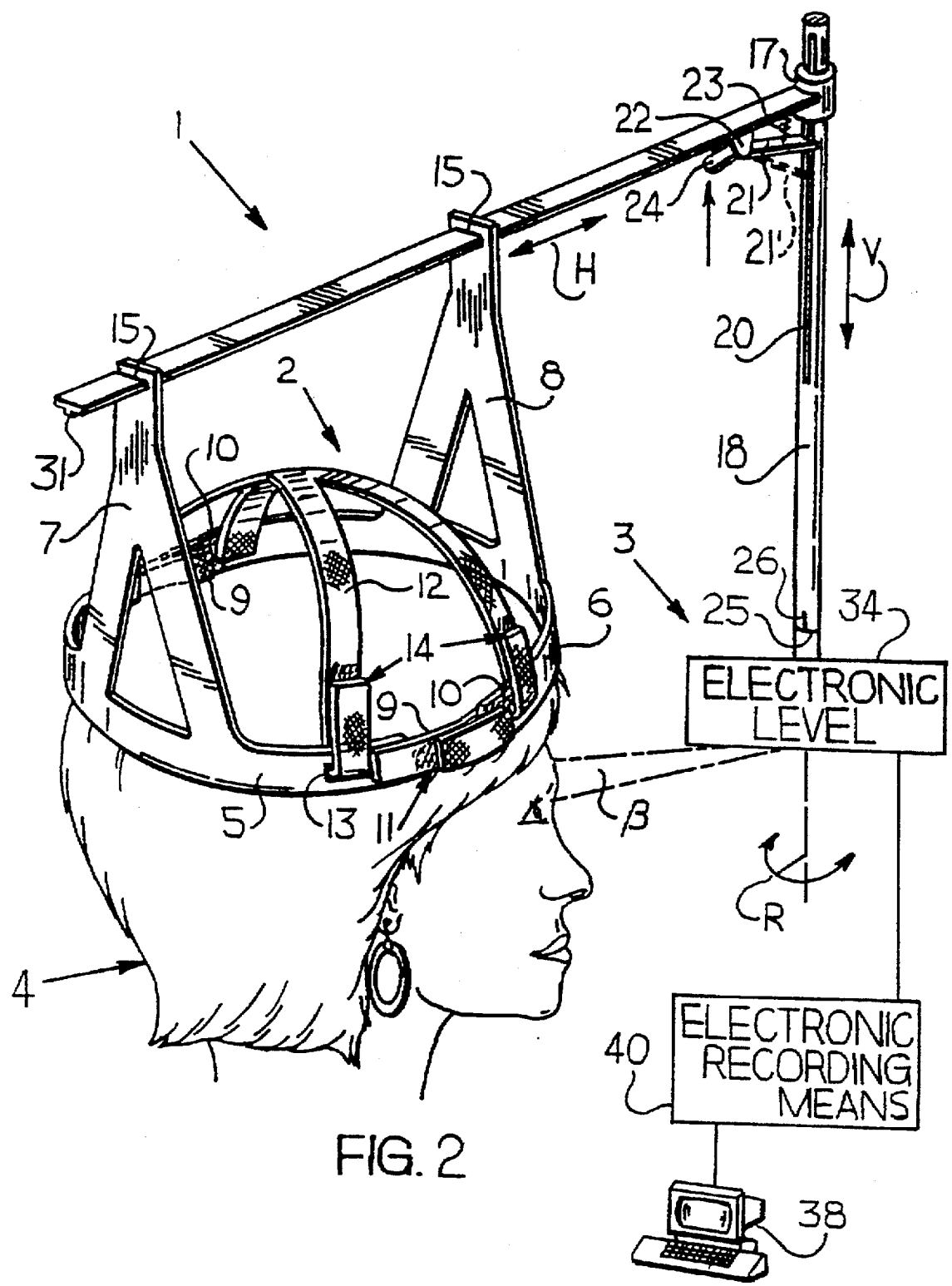

Although the invention is described here with reference to a spirit level instruments which provides an analog indication of the position, it will be apparent to the skilled person that any position indicating device readable by the user can be considered suitable for use. Envisaged here are electronic, thus digital, instruments such as an electronic level instrument as described in the European patent no. 0 349 074, or other type of position-sensitive electronic element, such as for example a mercury switch. FIG. 2 shows an electronic level instrument represented by block 34 suspended from the suspension rod 18. Use can then be made herein of an electronic indicator or an auditive signal. What is important is that the indication of the position is clearly observable for the user, so that the most direct possible feedback of the position of the part of the body for exercising is obtained, and that the sampling of the position-indicating electronic signal is performed sufficiently frequently to ensure a uniformly progressing quasi-analog indication of the position.

In addition to the shown spirit level instrument 19 a second position-indicating instrument, or second spirit level instrument 36, can further be suspended on the other side of the strip 16, which instrument cannot be seen by the user himself but on which a supervisor can check the progress of the exercises, as shown in FIG. 1. In the case use is made of electronic position-indicating means the exercise can also be supervised from a distance, wherein for example an output signal from the electronic level is sent to a computer terminal 38 and displayed there, as shown in FIG. 2. It is also possible to store the electronic output signals in electronic manner, such as with electronic recording means represented by block 40 in FIG. 2, and to analyze the exercise afterward in light thereof.

Because the training device according to the invention provides the user with a direct feedback of the position of a body part in response to a signal transmitted by the equilibrium organs, possible equilibrium disturbance can be made visible, analyzed and optionally corrected in rapid and simple manner.

I claim:

1. A training device for performing equilibrium exercises, comprising a fitting means for stably fitting the device to a part of the body of a user and a position indicating means connected to the fitting means,
    wherein the position indicating means is viewable by the user during normal use of the device when the fitting means is positioned on a part of the body of the user and visually indicates the position of the device, and
    wherein the position indicating means includes a spirit level instrument viewable by the user during normal use with the fitting means on the body.

2. The training device as claimed in claim 1, wherein the fitting means is configured to be worn on the head of the user.

3. The training device as claimed in claim 2, wherein the fitting means further includes:
    a head-band configured to be adjustable to fit the head of the user of the device;
    at least two substantially rigid uprights extending from the head-band, the at least two uprights each defining a slot at the end of each of the at least two uprights; and
    a strip slidably received in the slots defined by the at least two uprights,
    wherein the strip permits the distance between the spirit level instrument and the head of the user to be varied.

4. The training device as claimed in claim 1, wherein the spirit level instrument is vertically adjustable relative to the fitting means so that the spirit level instrument is positionable at a selected height relative to the body of the user.

5. The training device as claimed in claim 1, wherein the spirit level instrument further includes a damping means controlling the response speed of the spirit level instrument.

6. The training device as claimed in claim 5, wherein the damping means is a highly viscous liquid in the spirit level instrument damping the response speed of the spirit level instrument.

7. The training device as claimed in claim 5, wherein the damping means is an upwardly curved transparent tube body partially filled with liquid and having an air bubble therein, and wherein the tube body is positioned within the spirit level instrument.

8. The training device as claimed in claim 1, wherein the spirit level instrument is an electronic level.

9. The training device as claimed in claim 8, further including electronic recording means connected to the electronic level for electronically recording the indicated position.

10. The training device as claimed in claim 9, wherein the electronic recording means includes a computer terminal placed at a distance from the training device.

11. The training device as claimed in claim 1, further including a second spirit level instrument suspended with and facing opposite the first spirit level instrument.

12. The training device as claimed in claim 1, wherein the spirit level instrument is suspended from the fitting means by a suspension rod, and wherein the spirit level instrument is rotatable about a longitudinal axis of the suspension rod and about an axis substantially transverse to the longitudinal axis of the suspension rod.

13. A training device for performing equilibrium exercises, comprising:
   a fitting means for stably fitting the device to the head of a user; and
   a position indicating means connected to the fitting means,
   wherein the position indicating means is viewable by the user during normal use of the device when the fitting means is positioned on the head of the user and visually indicates the position of the device,
   wherein the position indicating means includes a spirit level instrument viewable by the user during normal use of the device with the fitting means on the head of the user, and
   wherein the spirit level instrument includes a damping means controlling the response speed of the spirit level instrument.

14. The training device as claimed in claim 13, wherein the damping means is a highly viscous fluid in the spirit level instrument damping the response speed of the spirit level instrument.

15. The training device as claimed in claim 13, wherein the damping means is an upwardly curved transparent tube body partially filled with liquid and having an air bubble therein, and wherein the tube body is positioned within the spirit level instrument.

16. The training device as claimed in claim 13, wherein the spirit level instrument is an electronic level.

17. The training device as claimed in claim 13, wherein the fitting means further includes:
   a head-band configured to be adjustable to fit the head of the user of the device;
   at least two substantially rigid uprights extending from the head-band, the at least two uprights each defining a slot at the end of each of the at least two uprights; and
   a profiled strip slidably received in the slots defined by the at least two uprights,
   wherein the profiled strip permits the distance between the spirit level instrument and the head of the user to be varied.

18. The training device as claimed in claim 13, wherein the spirit level instrument is vertically adjustable relative to the fitting means so that the spirit level instrument is positionable at a selected height relative to the head of the user.

19. The training device as claimed in claim 13, wherein the spirit level instrument is suspended from the fitting means by a suspension rod, and wherein the spirit level instrument is rotatable about a longitudinal axis of the suspension rod and about an axis substantially transverse to the longitudinal axis of the suspension rod.

20. A training device for performing equilibrium exercises, comprising:
   a head-band configured to be adjustable to fit the head of a user of the device;
   at least two substantially rigid uprights extending from the head-band, the at least two uprights each defining a slot at the end of each of the at least two uprights;
   a strip slidably received in the slots defined by the at least two uprights;
   a suspension rod connected at one end to the strip; and
   a spirit level instrument located at the other end of the suspension rod and viewable by the user during normal use when the device is positioned on the head of the user and visually indicates the position of the device,
   wherein the suspension rod is vertically adjustable relative to the strip so that the spirit level instrument is positionable at a selected height relative to the head of the user, and
   wherein the spirit level instrument is rotatable about a longitudinal axis of the suspension rod and about an axis substantially transverse to the longitudinal axis of the suspension rod.

* * * * *